(12) United States Patent
Lee

(10) Patent No.: US 8,764,793 B2
(45) Date of Patent: Jul. 1, 2014

(54) LEFT ATRIAL APPENDAGE OCCLUDER

(75) Inventor: Richard Lee, Lake Forest, IL (US)

(73) Assignee: Northwestern University, Evanston, IL (US)

( * ) Notice: Subject to any disclaimer, the term of this patent is extended or adjusted under 35 U.S.C. 154(b) by 71 days.

(21) Appl. No.: 13/494,632

(22) Filed: Jun. 12, 2012

(65) Prior Publication Data
US 2012/0323270 A1    Dec. 20, 2012

Related U.S. Application Data

(60) Provisional application No. 61/498,320, filed on Jun. 17, 2011.

(51) Int. Cl.
*A61B 17/08* (2006.01)
*A61D 1/00* (2006.01)

(52) U.S. Cl.
USPC .......................................... 606/213

(58) Field of Classification Search
CPC ..................... A61B 17/0057; A61B 17/12172; A61B 17/12122; A61B 2017/00575; A61B 17/12022; A61B 2017/00592; A61B 17/12186; A61B 17/1219; A61B 17/12159
USPC ................ 606/108, 191, 194, 198, 200, 213; 623/1.15, 1.24, 1.25, 1.36
See application file for complete search history.

(56) References Cited

U.S. PATENT DOCUMENTS

| | | | |
|---|---|---|---|
| 6,152,144 A | 11/2000 | Lesh et al. | |
| 6,551,303 B1 * | 4/2003 | Van Tassel et al. | 604/508 |
| 6,689,150 B1 * | 2/2004 | VanTassel et al. | 606/200 |
| 2005/0004652 A1 * | 1/2005 | van der Burg et al. | 623/1.12 |
| 2005/0216054 A1 * | 9/2005 | Widomski et al. | 606/213 |
| 2006/0136043 A1 | 6/2006 | Cully | |
| 2008/0215087 A1 * | 9/2008 | Pavcnik et al. | 606/213 |
| 2009/0093809 A1 * | 4/2009 | Anderson et al. | 606/41 |
| 2011/0054515 A1 | 3/2011 | Bridgeman | |
| 2011/0208233 A1 * | 8/2011 | McGuckin et al. | 606/200 |

FOREIGN PATENT DOCUMENTS

| | | |
|---|---|---|
| WO | WO 00/27292 | 5/2000 |
| WO | WO 2007/083288 | 7/2007 |

OTHER PUBLICATIONS

Blackshear and Odell. "Appendage obliteration to reduce stroke in cardiac surgical patients with atrial fibrillation." Ann Thorac Surg (1996) vol. 61 (2) pp. 755-759.

(Continued)

*Primary Examiner* — Katherine M Shi
(74) *Attorney, Agent, or Firm* — Klintworth & Rozenblat IP LLC

(57) ABSTRACT

Systems and methods for occluding a left atrial appendage are disclosed. A left atrial appendage may be covered with a first occluder device to obstruct the passage of blood out of the left atrial appendage. The first occluder device may include an expandable member, a cover attached to and covering an end of the expandable member, and a one-way valve disposed in the cover. The cover may form a flexible pocket between the cover and the expandable member. The cover may be made of bioprosthetic material. A second occluder device may also be disposed within the left atrial appendage by inserting the second occluder device through the one-way valve in the cover of the first occluder device. The second occluder device may be used to stretch the left atrial appendage to obliterate the left atrial appendage.

16 Claims, 14 Drawing Sheets

(56) References Cited

OTHER PUBLICATIONS

Heist et al. "Analysis of the left atrial appendage by magnetic resonance angiography in patients with atrial fibrillation." Heart Rhythm (2006) vol. 3 (11) pp. 1313-1318.
Katz et al. "Surgical left atrial appendage ligation is frequently incomplete: a transesophageal echocardiographic study." J Am Coll Cardiol (2000) vol. 36 (2) pp. 468-471.
Gorodnitskiy et al. "A novel approach to left atrial appendage exclusion: the Watchman device." Cardiol Rev (2010) vol. 18 (5) pp. 230-233.
Holmes et al. "Percutaneous closure of the left atrial appendage versus warfarin therapy for prevention of stroke in patients with atrial fibrillation: a randomised non-inferiority trial." Lancet (2009) vol. 374 (9689) pp. 534-542.
Onalan and Crystal. "Left atrial appendage exclusion for stroke prevention in patients with nonrheumatic atrial fibrillation." Stroke (2007) vol. 38 (2 Suppl) pp. 624-630.
Stergiopoulos et al. "Thrombus Formation After Successful Stapler Exclusion of the Left Atrial Appendage." J Am Coll Cardiol (2010) vol. 55 (4) pp. 379-379.
Salzberg et al. "Left atrial appendage clip occlusion: early clinical results." J Thorac Cardiovasc Surg (2010) vol. 139 (5) pp. 1269-1274.
Maisel. "Left atrial appendage occlusion-closure or just the beginning?" N Engl J Med (2009) vol. 360 (25) pp. 2601-2603.
Feinberg et al. "Prevalence, age distribution, and gender of patients with atrial fibrillation." Analysis and implications. Arch Intern Med (1995) vol. 155 (5) pp. 469-473.
Wolf et al. "Atrial Fibrillation as an independent risk factor for stroke—the Framingham Study." Stroke (1991) vol. 22 (8) pp. 938-988.
Olsson et al. "Atrial fibrillation and risk of clinical events in chronic heart failure with and without left ventricular systolic dysfunction—Results from the Candesartan in Heart failure-Assessment of Reduction in Mortality and Morbidity (CHARM) program." J Am Coll Cardiol (2006) vol. 47 (10) pp. 1997-2004.
Frost, L., G. Engholm, et al (2000) "Incident stroke after discharge from the hospital with a diagnosis of atrial fibrillation." American Journal of Medicine 108 (1): 36-40.
Salzberg, S.P., A. Plass, et al (2008). "Left Atrial Appendage Occlusion: Early Clinical Results with a New Clip." Circulation 118(18) S860-S860.
McCarthy, P.M., R. Lee et al (2010). "Occlusion of canine atrial appendage using an expandable silicone band." J Thorac Cardiovasc Surg.
Kanderian, A.S., A.M. Gillinov, et al. (2008) "Success of surgical left atrial appendage closure." Journal of hte American College of Cardiology 52(11): 924-929.
PCT Invitation to Pay Additional Fees and, Where Applicable, Protest Fee; Mailed Sep. 11, 2012.

* cited by examiner

US 8,764,793 B2

LEFT ATRIAL APPENDAGE OCCLUDER

RELATED APPLICATIONS

The disclosure is a utility patent application claiming priority to and the benefit of U.S. provisional patent application Ser. No. 61/498,320, entitled Left Atrial Appendage Occluder, filed on Jun. 17, 2011, which is hereby incorporated by reference in its entirety.

FIELD OF THE DISCLOSURE

The disclosure relates to systems and methods for occluding or obliterating a left atrial appendage.

BACKGROUND OF THE DISCLOSURE

Atrial fibrillation (AF) is a form of abnormal heart rhythm (often referred to as cardiac arrhythmia), and involves the muscles of the upper two chambers of the heart (the atria) quivering rather than contracting in a more coordinated manner. As many as 6 million people in the United States suffer from AF, and may be candidates for atrial appendage intervention. AF is the second leading cause of stroke in the United States and may account for nearly one-third of strokes in the elderly. As our population continues to age, this problem may become even more prevalent.

In greater than 90% of cases where a blood clot (thrombus) is found in the AF patient, the clot develops in the left atrial appendage (LAA) of the heart. The LAA is a pouch of heart muscle attached to the left atrium. Removal of the LAA may result in a reduction of the incidence of stroke in AF patients, and there is growing interest in both surgical and endovascular methods to remove the LAA.

The literature on the correlation between the LAA, thrombus formation, and stroke is largely based on a number of individual cases. While the pathophysiology of thrombus formation in the LAA remains poorly understood, these studies suggest that there exists an increased risk for thrombus formation when closure of the LAA is unsuccessful. Excision appears superior to other methods such as stapler or suture exclusion in patients undergoing cardiac surgery, but is not always practical. In an internal review of 49 patients, failure was found in 40% of cases after surgical LAA elimination.

New devices to percutaneously occlude the LAA have been developed for stroke prophylaxis and seem promising. These new devices include the use of a clip to clamp the LAA shut, the use of a snare to wall off the LAA, the use of an umbrella device to expand the LAA, the use of a device which may close the LAA but not obliterate it, and the use of a device which may fill the LAA without closing it. Data on the safety and efficacy of these devices must be considered over time. These new devices are early in clinical trials and have several limitations. For instance, use of the clip to clamp the LAA shut may not get down to the base of the LAA, may leave a residual stump or leak, may result in a clot forming, and may require open surgery. Use of the snare may leave a residual stump or leak, may be less controlled, and may not be possible if adhesions are located around the heart. Use of the umbrella device may require the patient to be on blood thinners since it is made out of a foreign material and does not occlude and obliterate the LAA simultaneously. Use of a device which may close the LAA without obliterating it, and use of a device which may obliterate the LAA without closing it are both incomplete solutions which may experience leakage, which may require blood thinners due to the use of synthetic materials, or which may experience other types of issues.

There is a need for an occluder system and method for occluding or obliterating the LAA while overcoming one or more issues of the existing systems and methods.

SUMMARY OF THE DISCLOSURE

In one embodiment, an occluder system for occluding a left atrial appendage comprises a first occluder device comprising an expandable member, a cover, and a valve. The first occluder device is configured to restrict blood flow out of the left atrial appendage. The cover is attached to the expandable member and covers an end of the expandable member. The valve is attached to the cover.

In another embodiment, an occluder system for occluding a left atrial appendage comprises an expandable member and a cover. The cover is made of bioprosthetic material and is attached to the expandable member covering an end of the expandable member.

In an additional embodiment, an occluder system for occluding a left atrial appendage comprises an expandable member and a cover. The cover covers an end of the expandable member. A first portion of the cover is fixedly attached to the expandable member and a second portion of the cover is detached from the expandable member thereby forming a flexible pocket between the cover and the expandable member.

In still another embodiment, a method of occluding a left atrial appendage is disclosed. In one step, a left atrial appendage is covered with a first occluder device to obstruct the passage of blood out of the left atrial appendage. In another step, a second occluder device is disposed within the left atrial appendage which stretches the left atrial appendage.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. The disclosure may be used on its own or combined with other technologies that seek to obstruct or obliterate the left atrial appendage (LAA). The embodiments of the disclosure described herein may be used openly, for patients undergoing cardiac surgery, or via a percutaneous approach as an alternative or supplement to anti-coagulation for the prevention of stroke.

Figure 1:
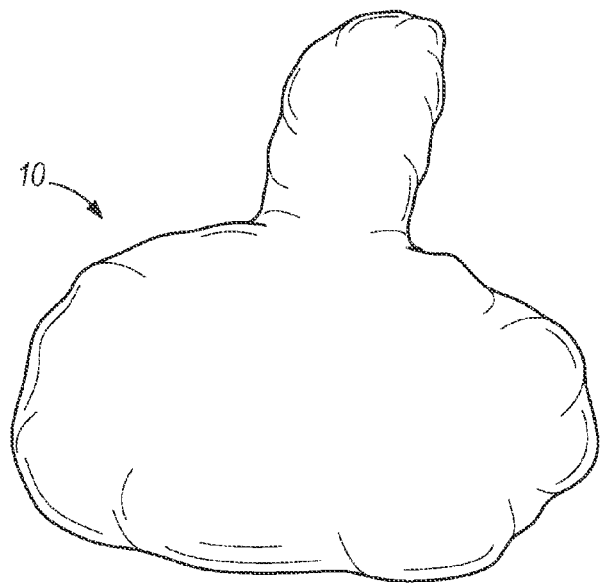
FIG. 1 illustrates an elevated view of one embodiment of a left atrial appendage.
Figure 2:
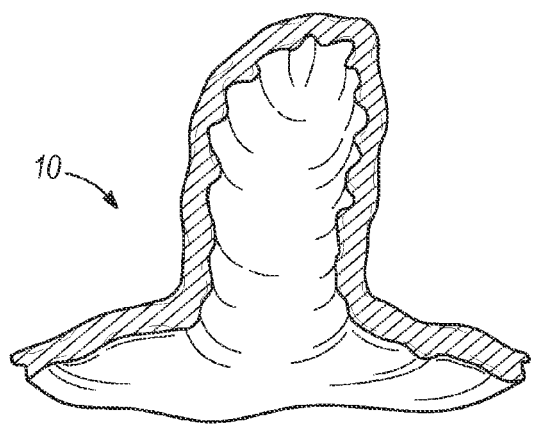
FIG. 2 illustrates a cross-sectional view through the left atrial appendage of FIG. 1.
Figure 3:
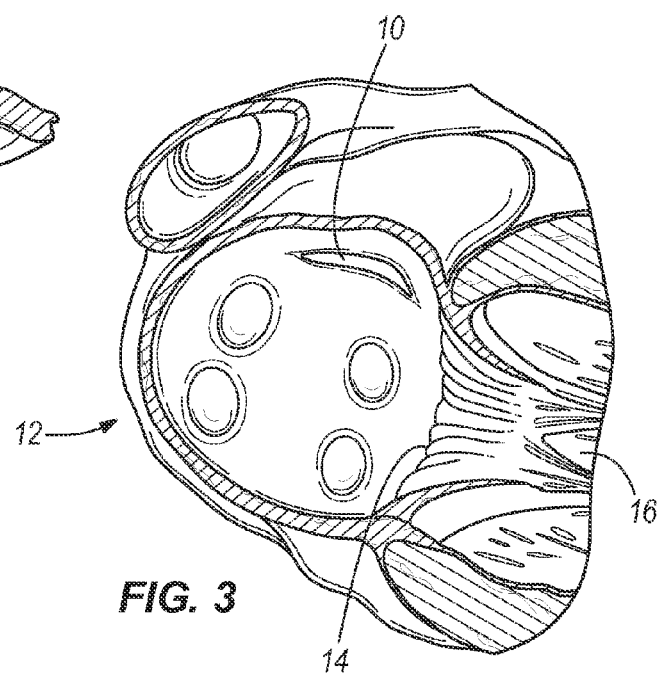
FIG. 3 illustrates a view from inside one embodiment of a left atrium.

FIG. 1 illustrates an elevated view of one embodiment of a LAA 10. FIG. 2 illustrates a cross-sectional view through the left atrial appendage 10 of FIG. 1. FIG. 3 illustrates a view from inside one embodiment of a left atrium 12. As shown collectively in FIGS. 1-3, the LAA 10 is a blind pouch that is part of the left atrium 12. When blood pools in conditions like atrial fibrillation, a clot may form in the LAA 10. When the clot breaks off, it may pass from the LAA 10, through the left atrium 12, through the mitral valve 14, and into the left ventricle 16. The clot may leave the heart via the aorta, and can travel to the brain to cause a stroke. It can be difficult to close the LAA 10 as human anatomy is highly variable and the shape of the LAA 10 is often irregular. Many prior devices and methods to exclude the LAA 10 often fail as they can leave a residual stump or leak. The devices and methods described below compensate for the variability and irregularity of the LAA 10 while greatly reducing the likelihood of a residual stump or leak.

Figure 4:
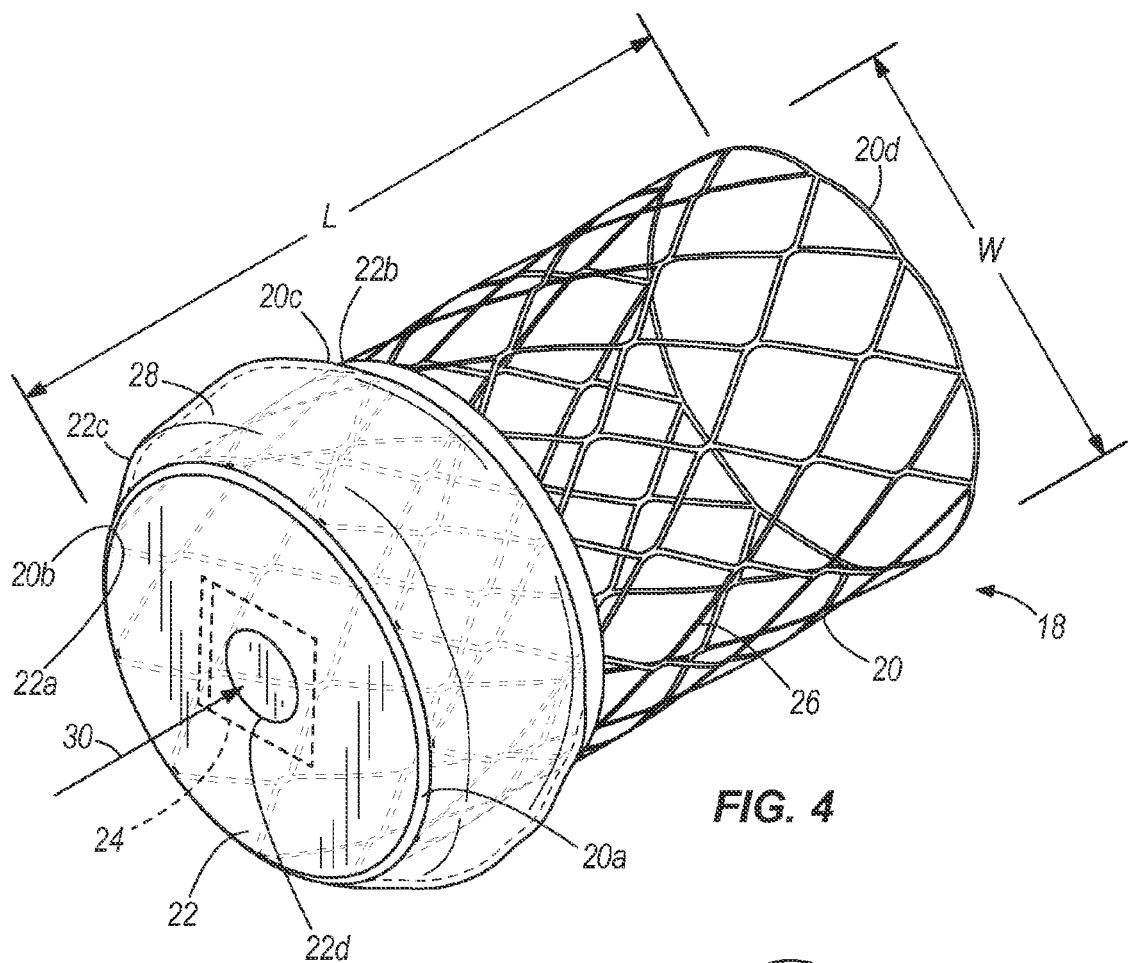
FIG. 4 illustrates a perspective view of one embodiment of a first occluder device for restricting blood flow out of a left atrial appendage.

FIG. 4 illustrates a perspective view of one embodiment of a first occluder device 18 for restricting blood flow out of an LAA. The first occluder device 18 comprises an expandable member 20, a cover 22, and a valve 24. The expandable member 20 comprises a stent comprising connected linked members 26 that are expandable into the hoop-shape shown in FIG. 4 from a constrained configuration. The stent may be similar to ones utilized in percutaneous valves and vascular endografts. In other embodiments, the expandable member 20 may comprise any type of expandable member such as a balloon, a sponge, or another type of expandable member which may utilize one or more attachment members such as a barb, a hook, or another type of attachment member for attaching the expandable member 20 to the LAA. The expandable member 20 may be made of stainless steel, Nitinol, or another expandable material. The expandable member 20 may be self-expandable or configured to expand using another type of expansion mechanism such as a balloon or other type of expansion mechanism.

The cover 22 covers an end 20a of the expandable member 20. The cover 22 may be made of bioprosthetic, Xenographic (i.e. pericardial or endovascular) material such as pericardium, bovine pericardium, equine pericardium, or other types of bioprosthetic material. The use of this material reduces the likelihood of blood clots and the need for the administration of blood thinners. In other embodiments, the cover 22 may be made of synthetic, non-thrombogenic material such as Polytetrafluoroethylene (PTFE), or other types of varying materials. One portion 22a of the cover 22 is fixedly attached to location 20b to and circumferentially around the end 20a of the expandable member 20. Another portion 22b of the cover 22 is fixedly attached to and circumferentially around the expandable member 20 at location 20c part-way along a length L of the expandable member 20 between the end 20a of the expandable member 20 and a second opposed end 20d of the expandable member 20. The ends 20a and 20d define the width W of the expandable member 20. Still another portion 22c of the cover 22 circumferentially covering the expandable member 20 is detached from the expandable member 20 in-between the locations 20b and 20c. Due to the cover 22 having portions 22a and 22b that are fixedly attached to the expandable member 20 and a portion 22c that is detached from the expandable member 20, a flexible circumferential pocket 28, which may be filled with blood in use, is formed between the cover 22 and the expandable member 20. In other embodiments, the cover 22 may be attached to the expandable member 20 in varying ways.

The valve 24 is attached to the cover 22. The valve 24 comprises a one-way valve for allowing blood to only flow in one direction 30 through the valve 24. The valve 24 may comprise a hinged door rotate-ably covering a hole 22d in the cover 22. In other embodiments, the valve 24 may comprise varying types of valves. In still other embodiments, the cover 22 may not contain a valve 24.

Figure 5:
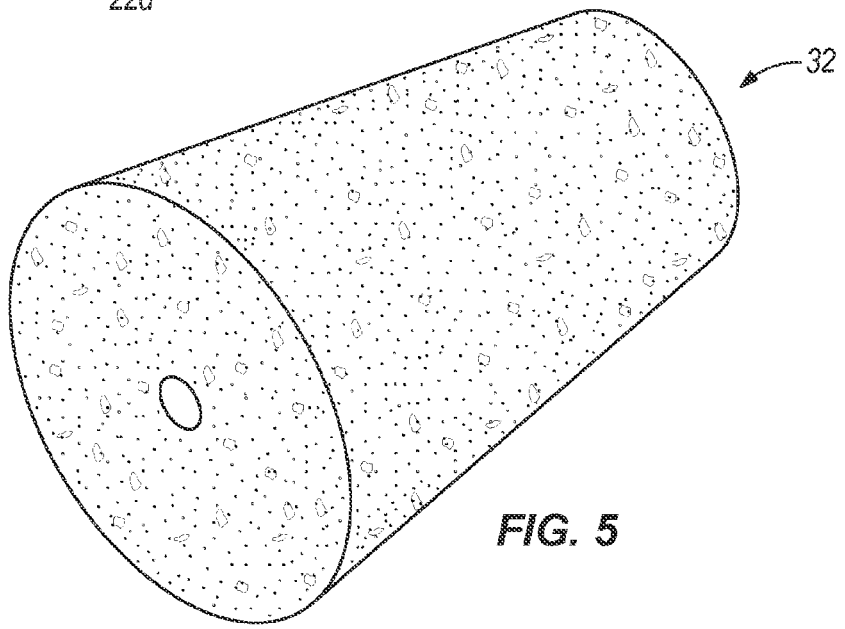
FIG. 5 illustrates a perspective view of one embodiment of a second occluder device for stretching a left atrial appendage from within the left atrial appendage without rupture.

FIG. 5 illustrates a perspective view of one embodiment of a second occluder device 32 for stretching the LAA from within the LAA without rupture. The second occluder device 32 may obliterate the LAA by expanding larger than the LAA. This may help patients in congestive heart failure by keeping the LAA full, as excision of the LAA may lead to a reduction of naturally occurring diuretics and result in fluid retention. The second occluder device 32 comprises a sponge which is configured to expand from an unexpanded state to an expanded state when filled with blood. The second occluder device 32 may be made of a material used for creating hemostasis and for percutaneously occluding undesirable arteries such as polyvinyl acetate, calcium alginate, or another type of material. As explained herein, the first and second occluder devices 18 and 32 of FIGS. 4 and 5 may be used together as an occluder system for occluding and obliterating the LAA. The second occluder device 32 may be in a conical shape and sized to fit, when configured in an unexpanded, dehydrated state, through the valve 24 of the first occluder device 18 of FIG. 4. The second occluder device 32 may expand when filled with blood while disposed inside the LAA to obliterate the LAA, fixedly secure the first occluder device 18 of FIG. 4 in place within the LAA, permanently prevent the valve 24 of the first occluder device 18 from opening, provide a back-up seal for the cover 22 of the first occluder device 18, seal off small perforations that could potentially occur, or achieve another function. In other embodiments, the second occluder device 32 may comprise a varying material, size, shape, or type.

Figure 6:
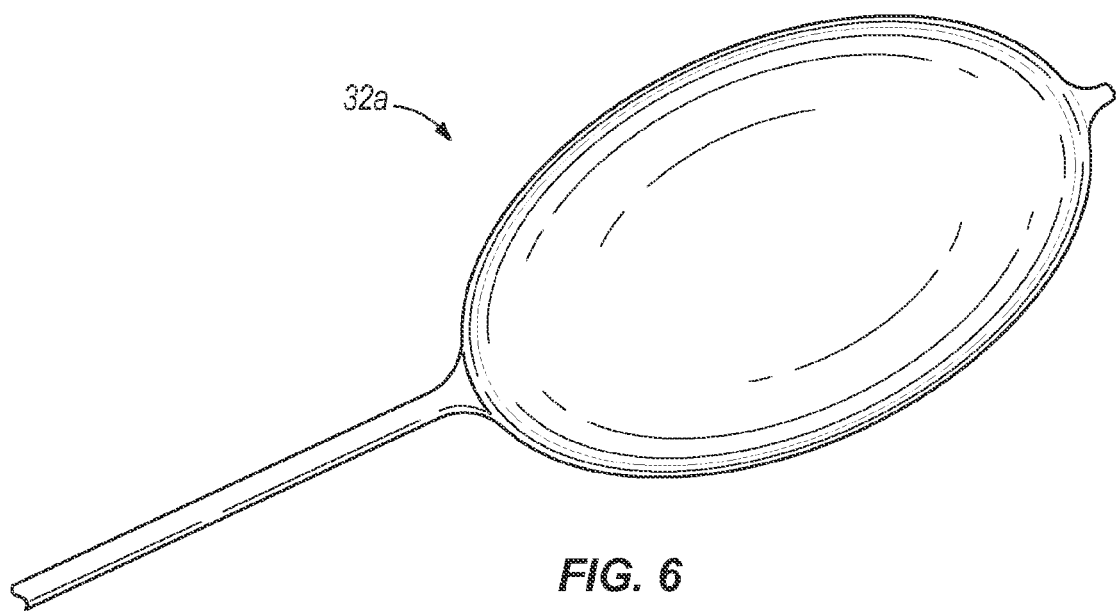
FIG. 6 illustrates a perspective view of another embodiment of a second occluder device for stretching a left atrial appendage from within the left atrial appendage without rupture.

FIG. 6 illustrates a perspective view of another embodiment of a second occluder device 32a for stretching the LAA from within the LAA without rupture. The second occluder device 32a may obliterate the LAA by expanding larger than the LAA. This may help patients in congestive heart failure by keeping the LAA full, as excision of the LAA may lead to a reduction of naturally occurring diuretics and result in fluid retention. The second occluder device 32a comprises a balloon which is configured to expand from an unexpanded state to an expanded state when filled with a liquid or gas such as CO2, saline, or another type of liquid, gas, or medium. The second occluder device 32a may be made of medical-grade silicone, rubber, latex, thermoplastic elastomers, or another material. The first and second occluder devices 18 and 32a of FIGS. 4 and 5 may be used together as an occluder system for occluding and obliterating the LAA. The second occluder device 32a may be sized to fit, when configured in an unexpanded state, through the valve 24 of the first occluder device 18 of FIG. 4. The second occluder device 32a may expand when filled with a liquid, gas, or medium while disposed inside the LAA to obliterate the LAA, fixedly secure the first occluder device 18 of FIG. 4 in place within the LAA, permanently prevent the valve 24 of the first occluder device 18 from opening, provide a back-up seal for the cover 22 of the first occluder device 18, seal off small perforations that could potentially occur, or achieve another function. In other embodiments, the second occluder device 32a may comprise a varying material, size, shape, or type.

Figure 7:
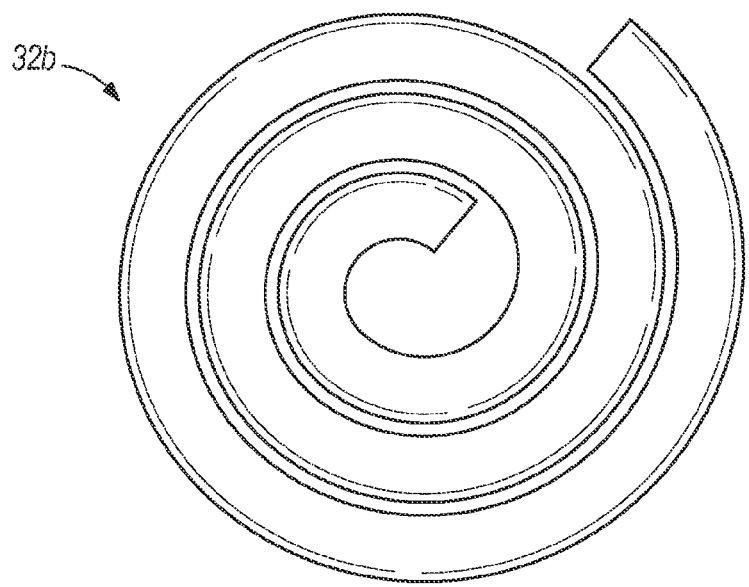
FIG. 7 illustrates a perspective view of another embodiment of a second occluder device for stretching a left atrial appendage from within the left atrial appendage without rupture.

FIG. 7 illustrates a perspective view of another embodiment of a second occluder device 32b for stretching the LAA from within the LAA without rupture. The second occluder device 32b may obliterate the LAA by filling the LAA. This may help patients in congestive heart failure by keeping the LAA full, as excision of the LAA may lead to a reduction of naturally occurring diuretics and result in fluid retention. The second occluder device 32b comprises an injectable material which may be injected through the valve 24 of the first occluder device 18 of FIG. 4 into the LAA. The second occluder device 32b may be made of gelfoam, medical-grade silicone, rubber, latex, thermoplastic elastomers, metal coils with or without Dacron coating, or another material. The first and second occluder devices 18 and 32b of FIGS. 4 and 5 may be used together as an occluder system for occluding and obliterating the LAA. The injection of the second occluder device 32b through the valve 24 of the first occluder device 18 of FIG. 4 into the LAA may fill the LAA to obliterate the LAA, fixedly secure the first occluder device 18 of FIG. 4 in place within the LAA, permanently prevent the valve 24 of the first occluder device 18 from opening, provide a back-up seal for the cover 22 of the first occluder device 18, seal off small perforations that could potentially occur, or achieve another function. In other embodiments, the second occluder device 32b may comprise a varying material, size, shape, or type.

Figure 8:
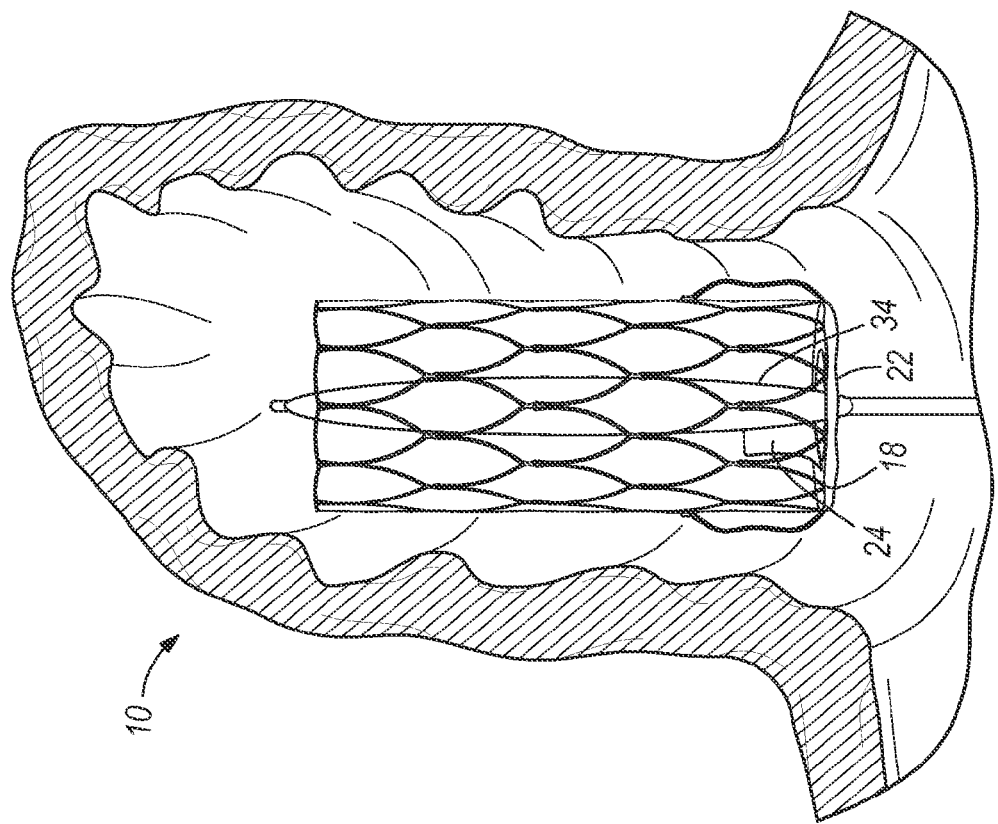
FIG. 8 illustrates a cut-away view of a left atrial appendage showing in one embodiment a delivery apparatus, which has been inserted through a valve in a cover of a first occluder device, disposing the first occluder device in an unexpanded state within the left atrial appendage.

FIGS. 8-18 illustrate cut-away views of an LAA 10 showing steps that may be followed using embodiments of the first and second occluder devices 18 and 32, 32a, and 32b of FIGS. 4-7 together to occlude and obliterate the LAA 10. FIG. 8 illustrates a cut-away view of the LAA 10 showing in one embodiment a delivery apparatus 34, which has been inserted through the valve 24 in the cover 22 of the first occluder device 18, disposing the first occluder device 18 in an unexpanded state within the LAA 10. The delivery apparatus 34 may comprise a catheter, a balloon catheter, a guide-wire, an expandable device, or another type of delivery apparatus known in the art. The first occluder device 18 may be delivered in a compressed, unexpanded state to within the LAA 10 percutaneously via either a trans-septal or retrograde approach using the delivery apparatus 34. In other embodiments, the first occluder device 18 may be delivered to within the LAA 10 during open surgery or using any delivery apparatus or method known in the art.

Figure 9:
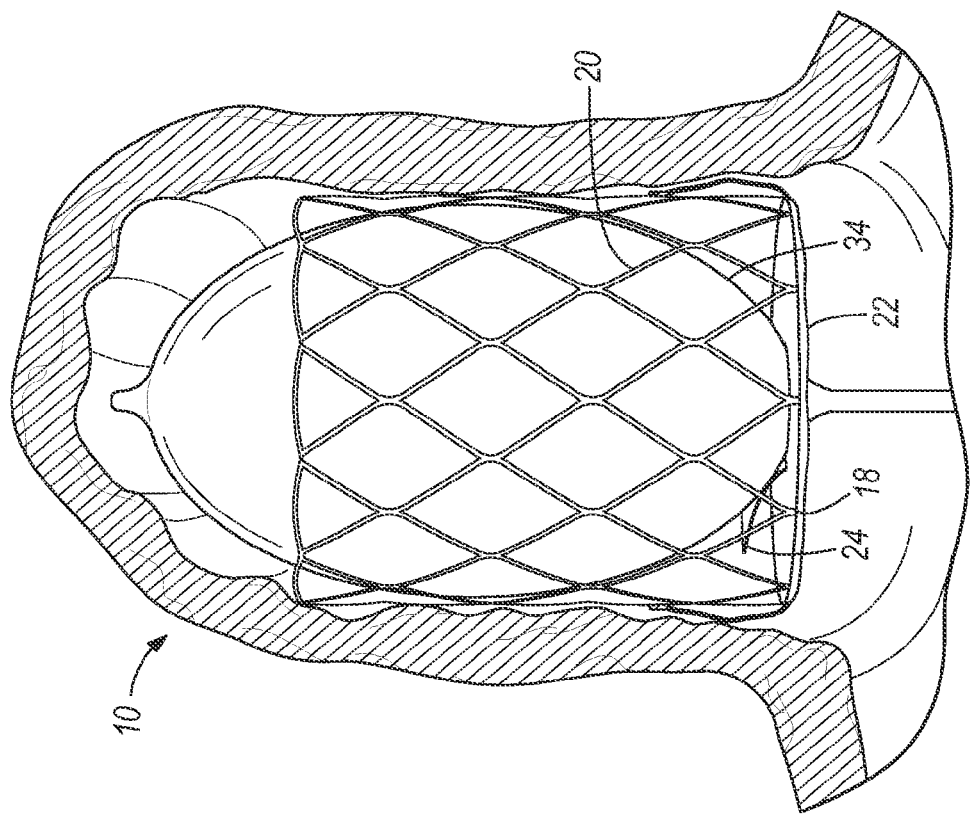
FIG. 9 illustrates a cut-away view of the left atrial appendage of FIG. 8 showing the delivery apparatus, inserted through the valve of the first occluder device, expanding the first occluder device into an expanded state within and against the left atrial appendage stretching the left atrial appendage so that the force of the left atrial appendage holds the first occluder device in place within the left atrial appendage.

FIG. 9 illustrates a cut-away view of the LAA 10 of FIG. 8 showing the delivery apparatus 34, inserted through the valve 24 of the first occluder device 18, expanding the first occluder device 18 into an expanded state within and against the LAA 10 stretching the LAA 10 so that the force of the LAA 10 holds the first occluder device 18 in place within the LAA 10. During the expansion process, the delivery apparatus 34 expands to expand the first occluder device 18 into the expanded state within and against the LAA 10. In this expanded state, the expandable member 20 of the first occluder device 18 is expanded against the LAA 10 and the cover 22 of the first occluder device 18 covers the LAA 10. In other embodiments, the first occluder device 18 may be self-expanded or expanded using varying expansion mechanisms to be secured within and against the LAA 10. As discussed previously, the cover 22 may be made of an anti-clogging material which reduces the likelihood of a blood-clot forming thereby reducing the necessity for blood thinners.

Figure 10:
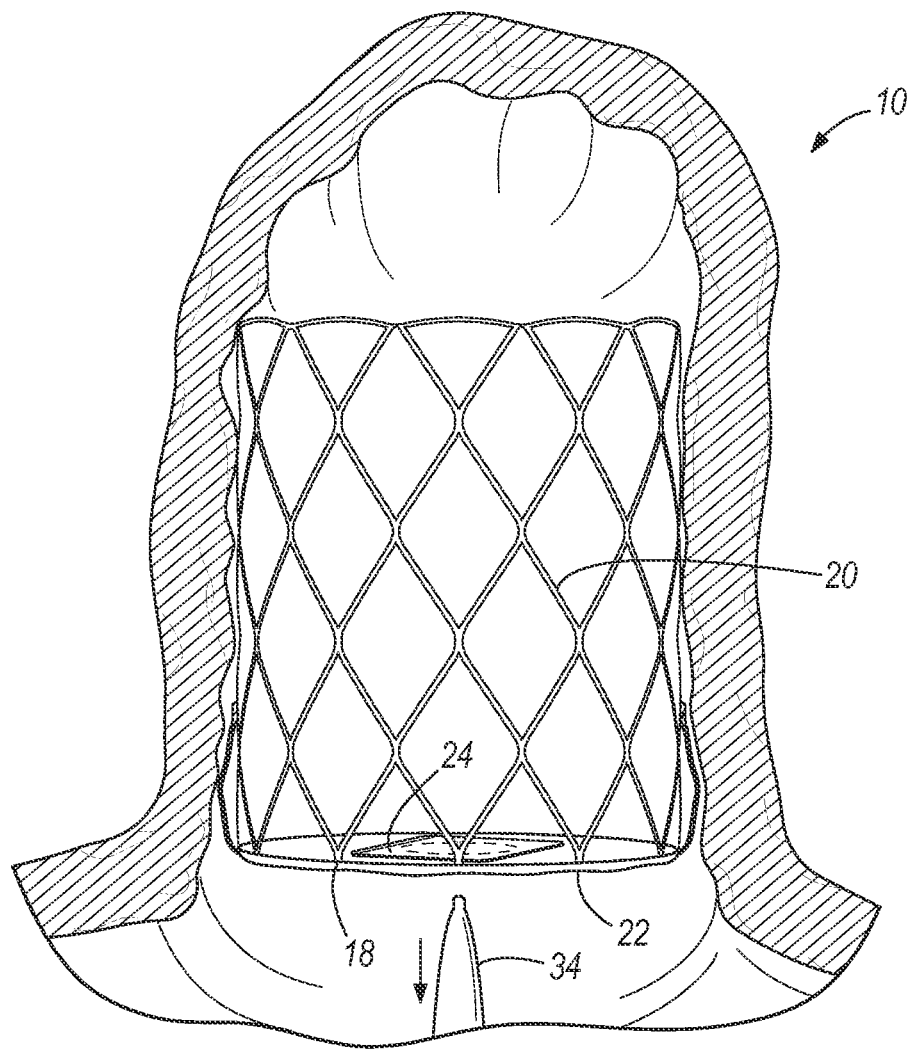
FIG. 10 illustrates a cut-away view of the left atrial appendage of FIG. 9 showing the delivery apparatus having been removed from the left atrial appendage leaving the first occluder device in the expanded state within and against the left atrial appendage with the valve in the cover of the first occluder device having closed.

FIG. 10 illustrates a cut-away view of the LAA 10 of FIG. 9 showing the delivery apparatus 34 having been removed from the LAA 10 leaving the first occluder device 18 in the expanded state within and against the LAA 10 with the valve 24 in the cover 22 of the first occluder device 18 having closed. In this expanded state, the expandable member 20 of the first occluder device 18 is expanded against the LAA 10 and the cover 22 of the first occluder device 18 covers the LAA 10.

Figure 11:
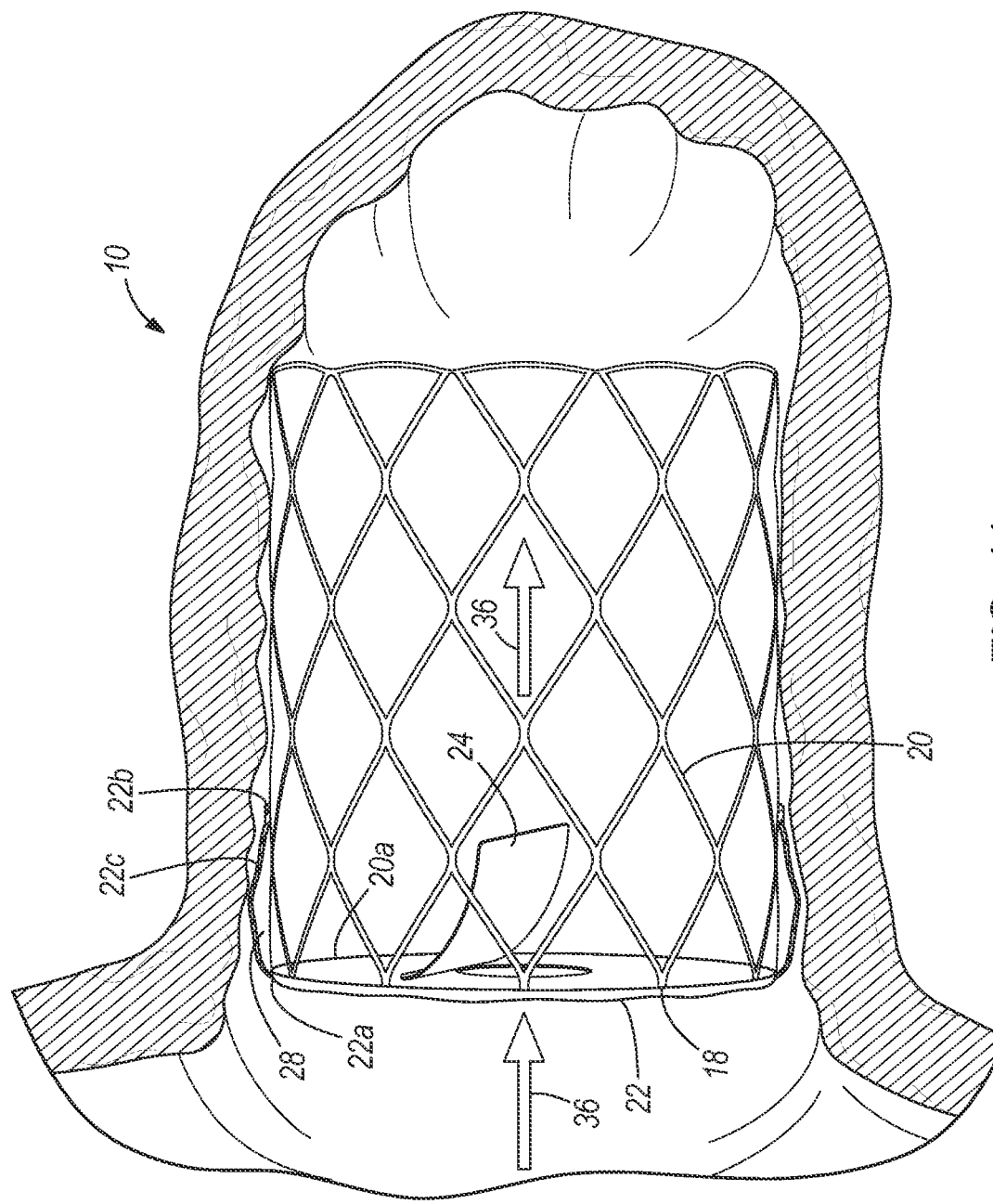
FIG. 11 illustrates a cut-away view of the left atrial appendage of FIG. 10 showing a flow of blood opening a valve in a cover of the expanded first occluder device and flowing into the left atrial appendage.

FIG. 11 illustrates a cut-away view of the LAA 10 of FIG. 10 showing a flow of blood 36 opening the valve 24 in the cover 22 of the expanded first occluder device 18 and flowing into the LAA 10. As the blood 36 flows into the LAA 10, the blood 36 passes through the expandable member 20 of the first occluder device 18 and pushes out the circumferential portion 22c of the cover 22 where the cover 22 is not fixed to the expandable member 20. Due to the cover 22 having circumferential portions 22a and 22b that are fixedly attached to the expandable member 20 along with the circumferential portion 22c of the cover 22 that is detached from the expandable member 20, the flow of blood fills in the flexible circumferential pocket 28 between the cover 22 and the expandable member 20 filling in any potential gaps between the LAA 10 and the cover 22. This helps to prevent leaks between the LAA 10 and the first occluder device 18, especially if the end 20a of the expandable member 20 is fixedly disposed within the LAA 10. In other embodiments, the end 20a of the expandable member 20 may be disposed outside the LAA 10 as long as portion 22b of the cover 22 is fixedly disposed against and within the LAA 10.

Figure 12:
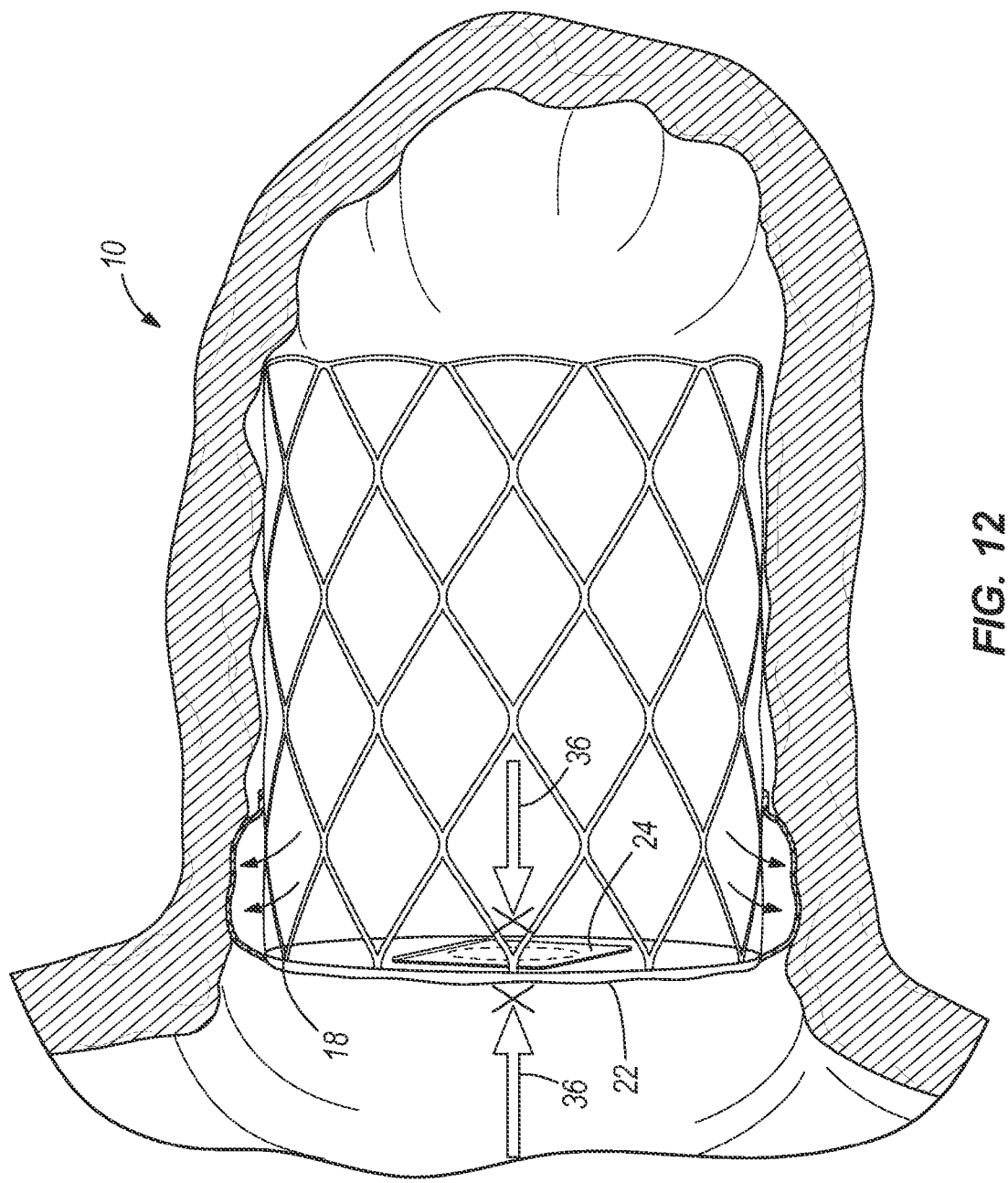
FIG. 12 illustrates a cut-away view of the left atrial appendage of FIG. 11 showing the valve of the cover of the first occluder device having closed due to the pressure of the blood within and outside the left atrial appendage having equalized.

FIG. 12 illustrates a cut-away view of the LAA 10 of FIG. 11 showing the valve 24 in the cover 22 of the first occluder device 18 having closed due to the pressure of the blood 36 within and outside the LAA 10 having equalized. In this closed position, the valve 24 prevents most if not all of the blood 36 from exiting the LAA 10. In addition, the valve 24 is beneficial in allowing devices to be inserted into the LAA 10 through the cover 22 when needed.

Figure 13:
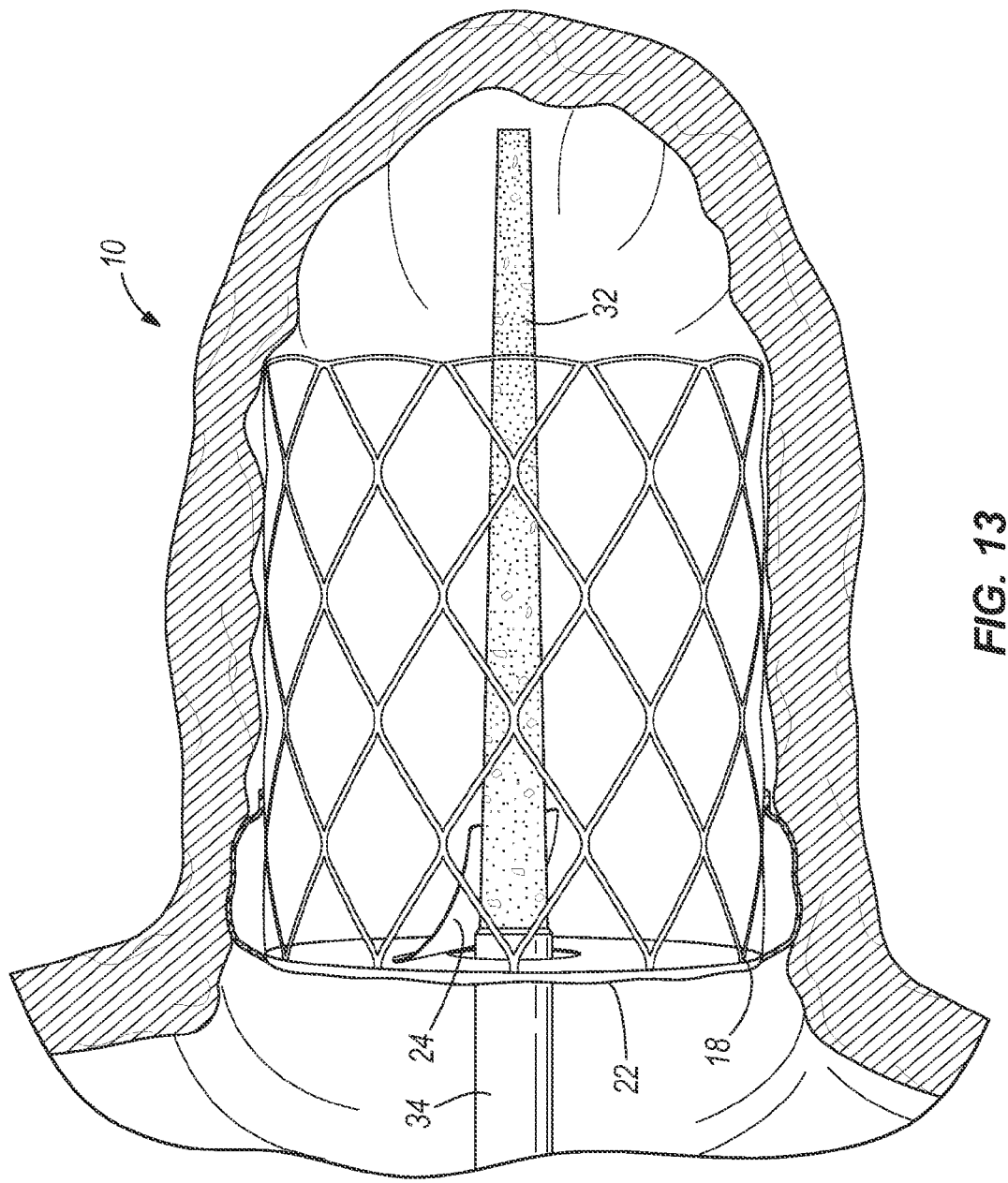
FIG. 13 illustrates a cut-away view of the left atrial appendage of FIG. 12 showing in one embodiment the delivery apparatus, which has been inserted through the valve of the first occluder device, delivering a second occluder device in an unexpanded state within the left atrial appendage inside of the first occluder device.

FIG. 13 illustrates a cut-away view of the LAA 10 of FIG. 12 showing in one embodiment the delivery apparatus 34, which has been inserted through the valve 24 of the first occluder device 18, delivering a second occluder device 32 in an unexpanded state within the LAA 10 inside of the first occluder device 18. The second occluder device 32 comprises a sponge.

Figure 14:
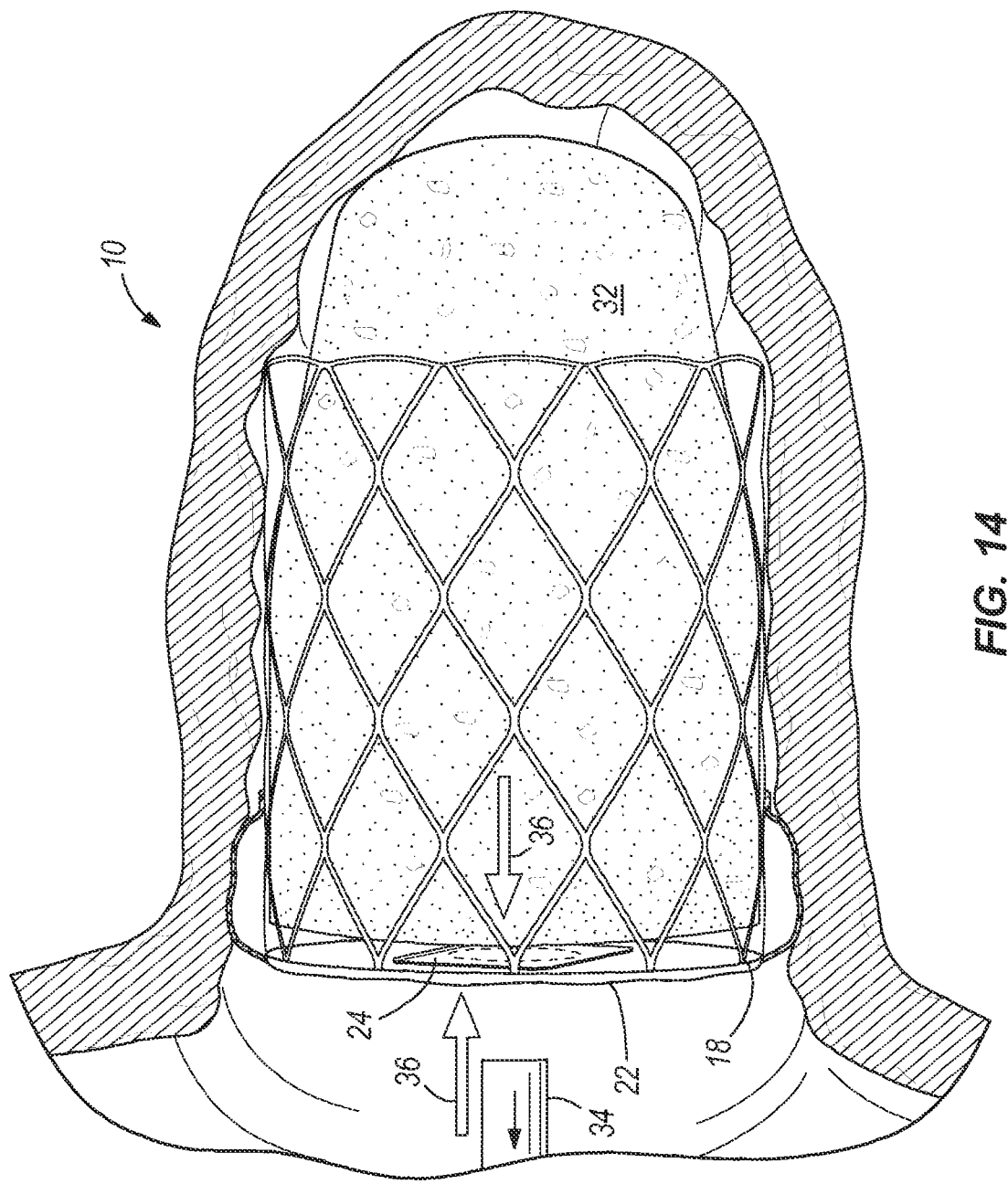
FIG. 14 illustrates a cut-away view of the left atrial appendage of FIG. 13 showing the second occluder device having expanded to an expanded state within the left atrial appendage inside of and against the first occluder device.

FIG. 14 illustrates a cut-away view of the LAA 10 of FIG. 13 showing the second occluder device 32 having expanded to an expanded state within the LAA 10 inside of and against the first occluder device 18. The delivery apparatus 34 has been retracted from the valve 24 in the cover 22 of the expanded first occluder device 18 allowing the valve 24 in the cover 22 to close due to the equalization of the pressure of the blood 36 within and outside the LAA 10. The second occluder device 32, comprising the sponge, has expanded against the first occluder device 18 due to the blood 36 filling the sponge. In this expanded position, the second occluder device 32 may obliterate the LAA 10 by expanding larger than the LAA 10, fixedly secure the first occluder device 18 in place within the LAA 10, permanently prevent the valve 24 of the first occluder device 18 from opening, provide a back-up seal for the cover 22 of the first occluder device 18, seal off small perforations that could potentially occur, or achieve one or more other functions. Use of the second occluder device 32 may further help patients in congestive heart failure by keeping the LAA full, as excision of the LAA may lead to a reduction of naturally occurring diuretics and result in fluid retention.

Figure 15:
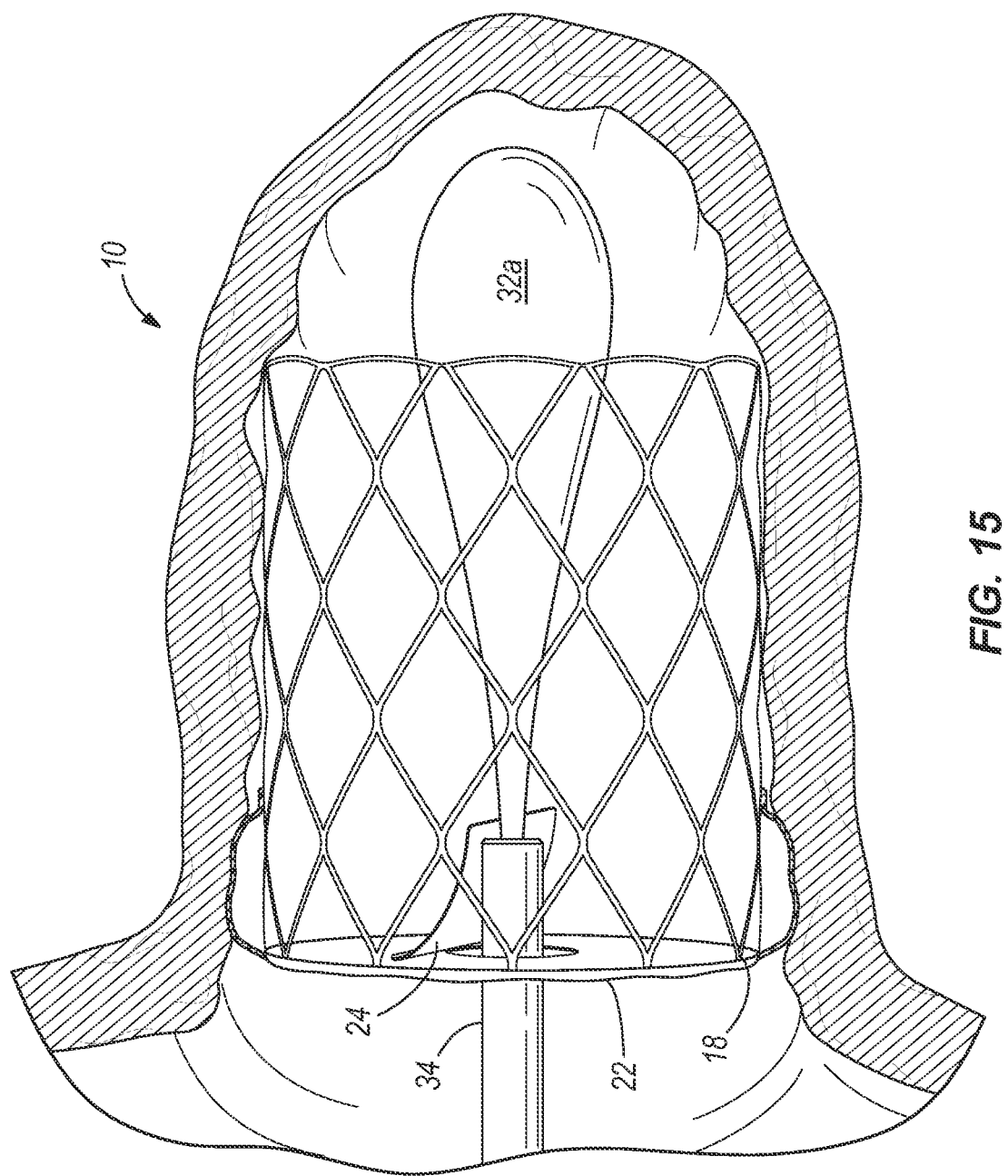
FIG. 15 illustrates a cut-away view of the left atrial appendage of FIG. 12 showing in another embodiment the delivery apparatus, which has been inserted through the valve of the first occluder device, delivering a different type of second occluder device in an unexpanded state within the left atrial appendage inside of the first occluder device.

FIG. 15 illustrates a cut-away view of the LAA 10 of FIG. 12 showing in another embodiment the delivery apparatus 34, which has been inserted through the valve 24 of the first occluder device 18, delivering a different type of second occluder device 32a in an unexpanded state within the LAA 10 inside of the first occluder device 18. The second occluder device 32a comprises a balloon.

Figure 16:
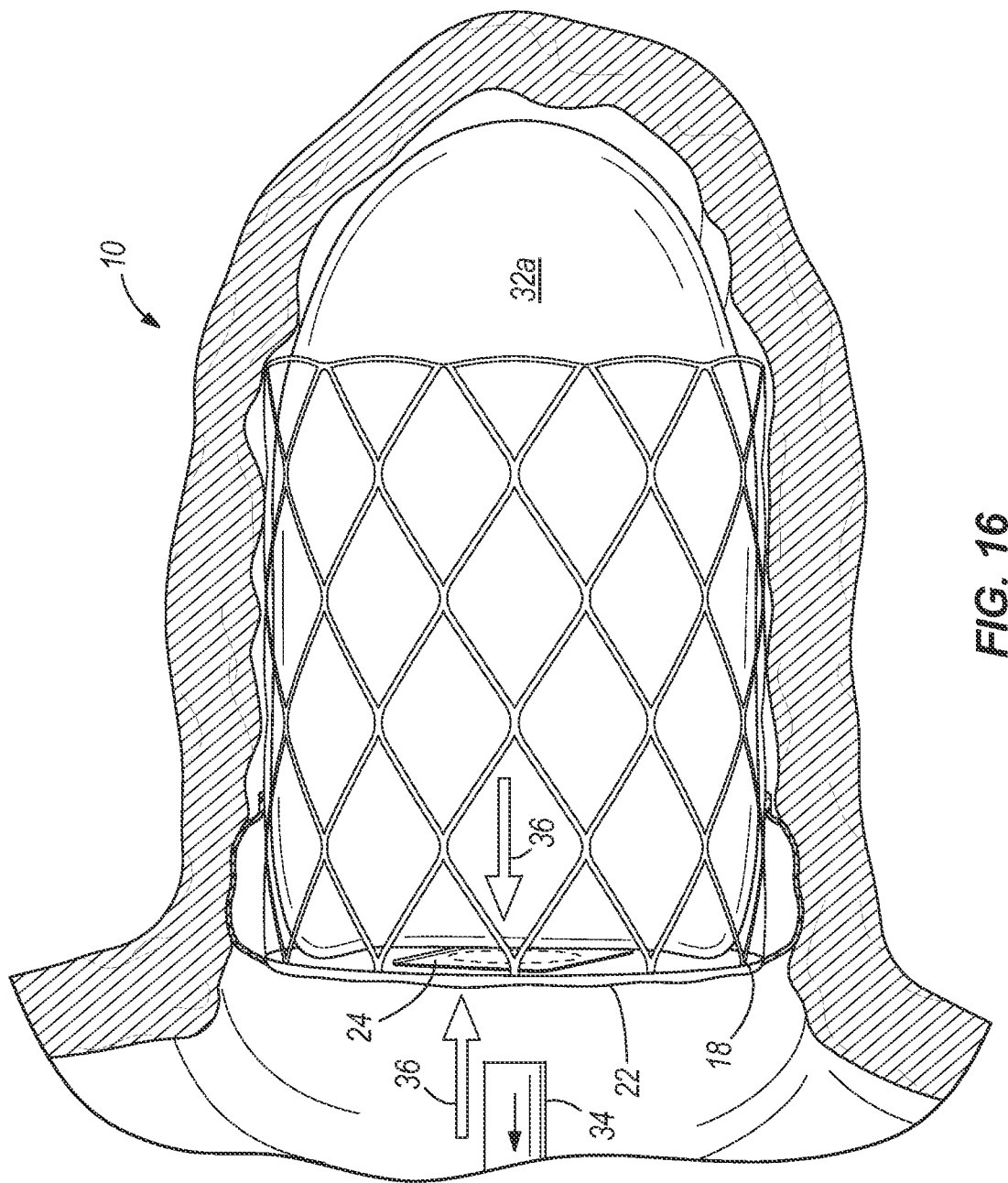
FIG. 16 illustrates a cut-away view of the left atrial appendage of FIG. 15 showing the second occluder device having been expanded to an expanded state within the left atrial appendage inside of and against the first occluder device.

FIG. 16 illustrates a cut-away view of the LAA 10 of FIG. 15 showing the second occluder device 32a having expanded to an expanded state within the LAA 10 inside of and against the first occluder device 18. The delivery apparatus 34 has been retracted from the valve 24 in the cover 22 of the expanded first occluder device 18 allowing the valve 24 in the cover 22 to close due to the equalization of the pressure of the blood 36 within and outside the LAA 10. The second occluder device 32a, comprising the balloon, has expanded against the first occluder device 18 due to the delivery apparatus 34 having filled the first occluder device 18 with a liquid, gas, or medium. In this expanded position, the second occluder device 32a may obliterate the LAA 10 by expanding larger than the LAA 10, fixedly secure the first occluder device 18 in place within the LAA 10, permanently prevent the valve 24 of the first occluder device 18 from opening, provide a back-up seal for the cover 22 of the first occluder device 18, seal off small perforations that could potentially occur, or achieve one or more other functions. Use of the second occluder device 32a may further help patients in congestive heart failure by keeping the LAA full, as excision of the LAA may lead to a reduction of naturally occurring diuretics and result in fluid retention.

Figure 17:
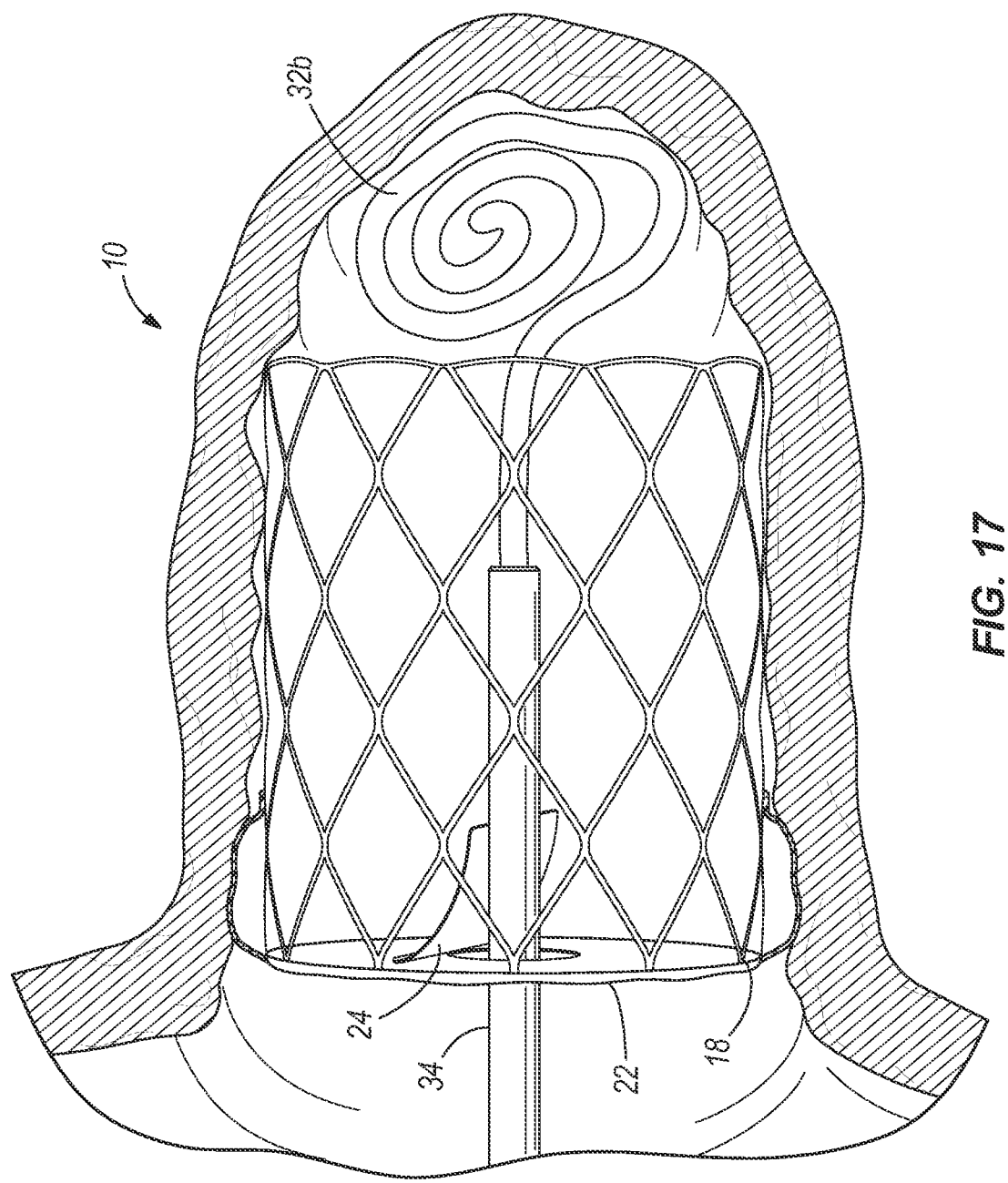
FIG. 17 illustrates a cut-away view of the left atrial appendage of FIG. 12 showing in one embodiment the delivery apparatus, which has been inserted through the valve in the cover of the first occluder device, delivering another different type of second occluder device within the left atrial appendage inside of the first occluder device.

FIG. 17 illustrates a cut-away view of the LAA 10 of FIG. 12 showing in one embodiment the delivery apparatus 34, which has been inserted through the valve 24 in the cover 22 of the first occluder device 18, delivering another different type of second occluder device 32b within the LAA 10 inside of the first occluder device 18. The second occluder device 32b comprises an injected material.

Figure 18:
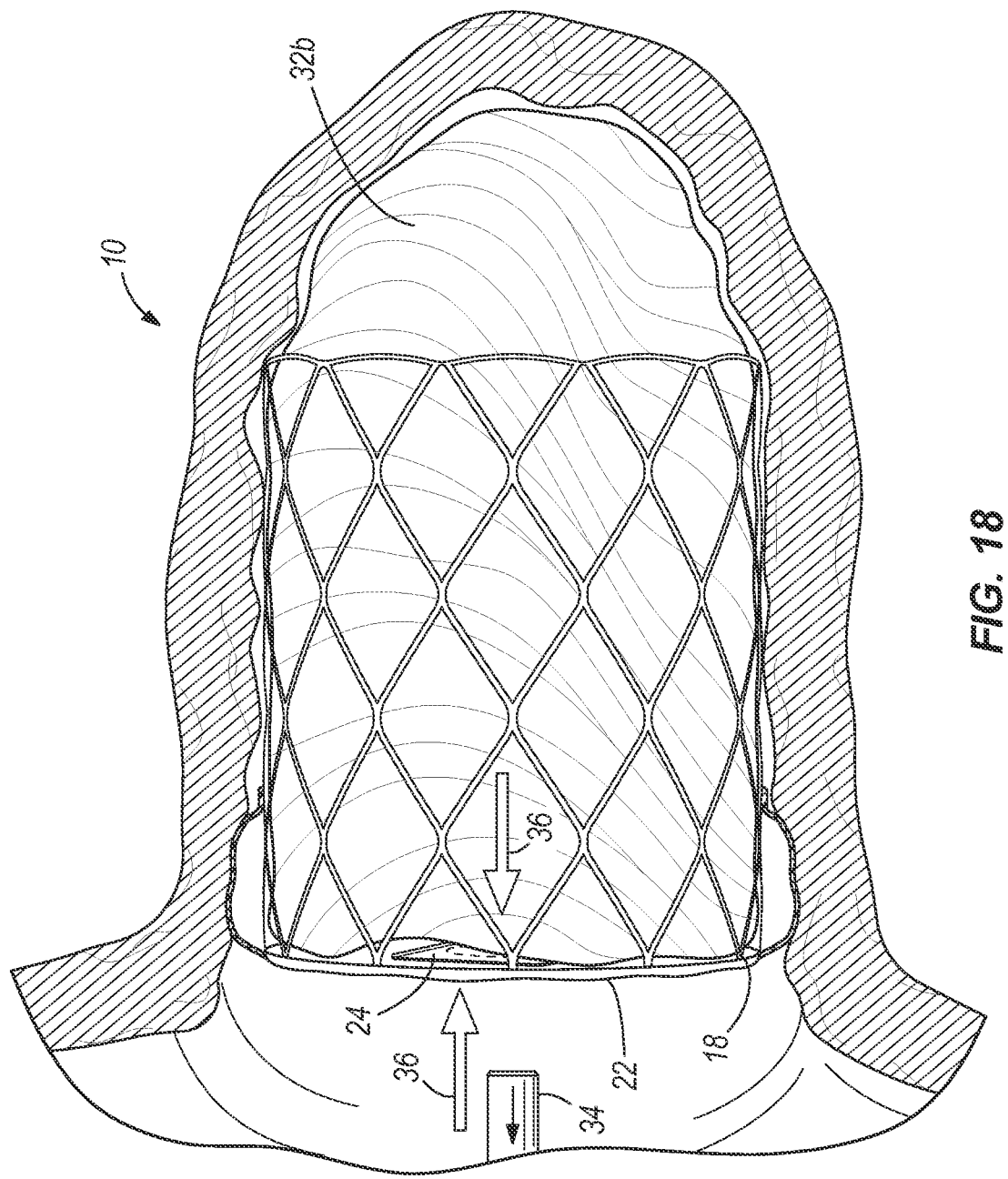
FIG. 18 illustrates a cut-away view of the left atrial appendage of FIG. 17 showing the second occluder device filling the left atrial appendage inside of and against the first occluder device.

FIG. 18 illustrates a cut-away view of the LAA 10 of FIG. 17 showing the second occluder device 32b filling the LAA 10 inside of and against the first occluder device 18. The delivery apparatus 34 has been retracted from the valve 24 in the cover 22 of the expanded first occluder device 18 allowing the valve 24 in the cover 22 to close due to the equalization of the pressure of the blood 36 within and outside the LAA 10. The second occluder device 32b, comprising the injected material, may obliterate the LAA 10 by filling the LAA 10 with the injected material, fixedly secure the first occluder device 18 in place within the LAA 10, permanently prevent the valve 24 of the first occluder device 18 from opening, provide a back-up seal for the cover 22 of the first occluder device 18, seal off small perforations that could potentially occur, or achieve one or more other functions. Use of the second occluder device 32b may further help patients in congestive heart failure by keeping the LAA full, as excision of the LAA may lead to a reduction of naturally occurring diuretics and result in fluid retention.

Figure 19:
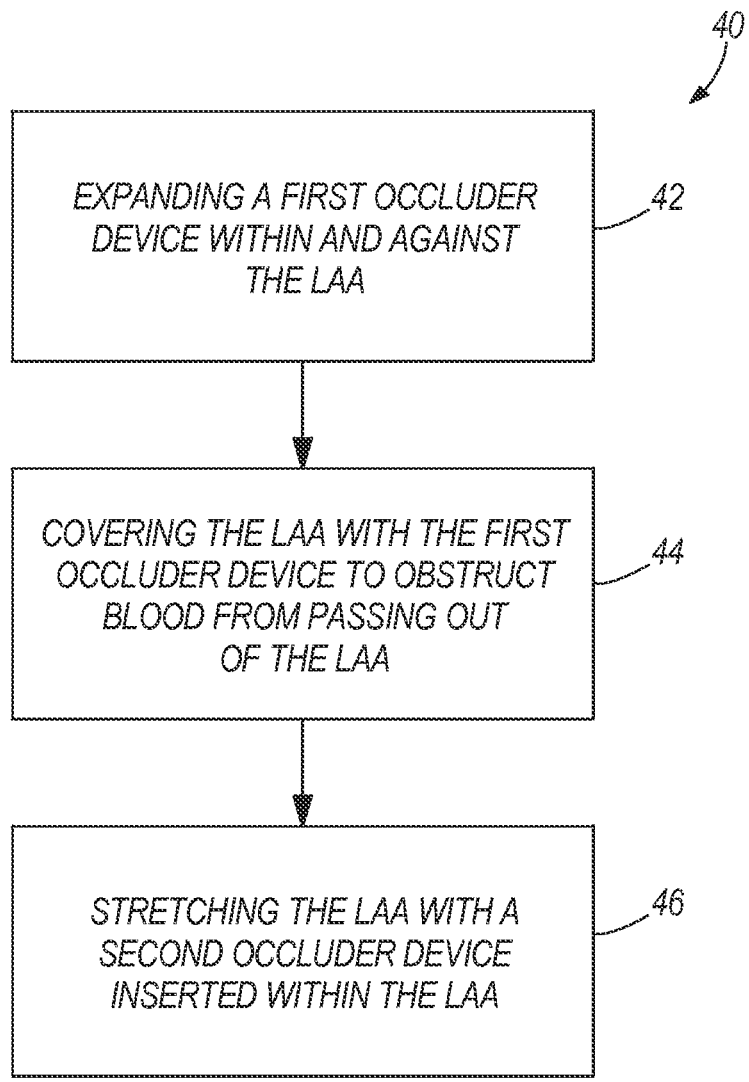
FIG. 19 is a flowchart illustrating one embodiment of a method of occluding a left atrial appendage.

FIG. 19 is a flowchart illustrating one embodiment of a method 40 of occluding or obliterating a LAA. In step 42, a first occluder device may be expanded within and against the LAA using a balloon, another expansion mechanism, or due to the first occluder device being self-expanding. In one embodiment, the first occluder device may comprise an expandable member, a cover attached to the expandable member covering an end of the expandable member, and a valve attached to the cover, and step 42 may comprise expanding the expandable member and the cover against the LAA. In one embodiment, the valve may comprise a one-way valve. In another embodiment, the cover may be made of a bioprosthetic material. In an additional embodiment, a first portion of the cover may be fixedly attached to the expandable member and a second portion of the cover may be detached from the expandable member thereby forming a flexible pocket between the cover and the expandable member. In one embodiment, the cover may be fixedly attached at a first location to the end of the expandable member, the cover may be fixedly attached to the expandable member at a second location part-way along a length of the expandable member between the end of the expandable member and a second opposed end of the expandable member, and the cover may be detached from the expandable member in-between the first location and the second location.

In step 44, the LAA is covered with the first occluder device to obstruct the passage of blood out of the LAA in order to occlude the LAA. In one embodiment, step 44 may comprise covering the LAA with a cover of the first occluder device. In another embodiment, step 44 may comprise disposing a first portion of a cover fixedly attached to an expandable member within and against the LAA, disposing at least part of a second portion of the cover detached from the expandable member within the LAA, and a flexible pocket formed between the second portion of the cover and the expandable member filling with blood to fill at least one gap between the LAA and the cover. In an additional embodiment, step 44 may comprise a one-way valve allowing blood to flow into the LAA but not out of the LAA.

In step 46, a second occluder device is disposed within the LAA and the LAA is stretched with the second occluder device. In one embodiment, step 46 may comprise inserting the second occluder device through a valve of the cover into the LAA. In one embodiment, the second occluder device may comprise a sponge, and step 46 may comprise the sponge expanding within and against the LAA as the sponge fills with blood thereby stretching the LAA. In another embodiment, the second occluder device may comprise a balloon, an expandable material, or an injectable material, and step 46 may comprise filling the balloon within the LAA with a gas, liquid, or other medium, expanding the expandable material within the LAA, or injecting the injectable material into the LAA. In another embodiment, step 46 may comprise expanding the second occluder device within and against the LAA to at least one of obliterate the LAA by filling the LAA with the second occluder device, prevent a valve in the cover of the first occluder device from opening, fixedly secure the first occluder device in place within the LAA, provide a back-up seal for the cover of the first occluder device, seal off small perforations that could potentially occur, or achieve another function. Use of the second occluder device may further help patients in congestive heart failure by keeping the LAA full, as excision of the LAA may lead to a reduction of naturally occurring diuretics and result in fluid retention. In other embodiments, one or more of the steps of the method 40 may be varied or not followed, or additional steps may be added.

One or more embodiments of the disclosure may reduce or eliminate one or more issues of the existing devices and methods for occluding or obliterating the LAA by: simultaneously allowing for the LAA to be both occluded and obliterated; reducing the likelihood of a leak out of the LAA; not requiring the use of blood-thinners; securely attaching to the LAA reducing the likelihood of subsequent dislodging; keeping the LAA full thereby helping patients in congestive heart failure by allowing for naturally occurring diuretics; providing an occlusion device which still allows for the LAA to be accessed after the LAA has been occluded; or by providing one or more additional benefits.

It should be understood, of course, that the foregoing relates to exemplary embodiments of the disclosure and that modifications may be made without departing from the spirit and scope of the disclosure as set forth in the following claims.

I claim:

1. An occluder system for occluding a left atrial appendage comprising:
    a first occluder device sized to cover the left atrial appendage to assist in preventing leaks in order to occlude the left atrial appendage and restrict blood flow out of the left atrial appendage comprising:
        an expandable member;
        a cover attached to the expandable member covering an end of the expandable member; and
        a valve attached to the cover;
    and a second occluder device configured to be delivered through the valve, the second occlude device comprising a means for simultaneously obliterating the left atrial appendage, by expanding the left atrial appendage or by filling the left atrial appendage, with the valve of the first occluder device shut as the first occluder device occludes and covers the left atrial appendage assisting in preventing leaks and restricting blood flow out of the left atrial appendage.

2. The occluder system of claim 1 wherein the expandable member comprises a stent.

3. The occluder system of claim 1 wherein the cover is made of bioprosthetic material.

4. The occluder system of claim 3 wherein the bioprosthetic material comprises pericardium, bovine pericardium, or equine pericardium.

5. The occluder system of claim 1 wherein a first portion of the cover is fixedly attached to the expandable member and a second portion of the cover is detached from the expandable member thereby forming a flexible pocket between the cover and the expandable member.

6. The occluder system of claim 5 wherein the cover is fixedly attached at a first location to the end of the expandable member, the cover is fixedly attached to the expandable member at a second location part-way along a length of the expandable member between the end of the expandable member and a second opposed end of the expandable member, and the cover is detached from the expandable member in-between the first location and the second location, wherein the flexible pocket is disposed outside of and around an outermost perimeter of the expandable member.

7. The occluder system of claim 1 wherein the valve comprises a one-way valve for allowing blood to flow in only one direction through the valve.

8. The occluder system of claim 1 wherein the valve comprises a hinged-door.

9. The occluder system of claim 1 wherein the means is for simultaneously expanding against the first occluder device as the means simultaneously obliterates the left atrial appendage, by expanding or filling the left atrial appendage, with the valve of the first occluder device shut as the first occluder device occludes and covers the left atrial appendage assisting in preventing leaks and restricting blood flow out of the left atrial appendage comprises a second occluder device.

10. The occluder system of claim 1 wherein the second occluder device is sized to fit through the valve in an unexpanded state.

11. The occluder system of claim 1 wherein the second occluder device comprises a sponge which expands when filled with blood.

12. The occluder system of claim 1 wherein the second occluder device comprises a balloon.

13. The occluder system of claim 1 wherein the second occluder device comprises an expandable material.

14. The occluder system of claim 1 wherein the second occluder device comprises an injectable material.

15. The occluder system of claim 1 wherein the means is for simultaneously obliterating the left atrial appendage, by expanding the left atrial appendage and by filling the left atrial appendage, with the valve of the first occluder device shut as the first occluder device occludes and covers the left atrial appendage assisting in preventing leaks and restricting blood flow out of the left atrial appendage.

16. The occluder system of claim 15 wherein the means is for simultaneously expanding against the first occluder device as the means simultaneously obliterates the left atrial appendage, by expanding the left atrial appendage and by filling the left atrial appendage, with the valve of the first occluder device shut as the first occluder device occludes and covers the left atrial appendage assisting in preventing leaks and restricting blood flow out of the left atrial appendage.

* * * * *